United States Patent
Mirkin et al.

(10) Patent No.: US 8,512,946 B2
(45) Date of Patent: Aug. 20, 2013

(54) COMPOSITE PARTICLES

(75) Inventors: Chad A. Mirkin, Wilmette, IL (US);
Savka I. Stoeva, San Diego, CA (US);
Fengwei Huo, Evanston, IL (US);
Jae-Seung Lee, Cambridge, MA (US)

(73) Assignee: Northwestern University, Evanston, IL (US)

( * ) Notice: Subject to any disclaimer, the term of this patent is extended or adjusted under 35 U.S.C. 154(b) by 687 days.

(21) Appl. No.: 12/063,206

(22) PCT Filed: Aug. 10, 2006

(86) PCT No.: PCT/US2006/031118
§ 371 (c)(1),
(2), (4) Date: Aug. 19, 2008

(87) PCT Pub. No.: WO2008/036075
PCT Pub. Date: Mar. 27, 2008

(65) Prior Publication Data
US 2010/0129793 A1    May 27, 2010

Related U.S. Application Data

(60) Provisional application No. 60/707,128, filed on Aug. 10, 2005.

(51) Int. Cl.
*C12Q 1/68* (2006.01)
*C07H 21/04* (2006.01)
*C12M 1/00* (2006.01)

(52) U.S. Cl.
USPC .................. 435/6.1; 435/283.1; 536/23.1

(58) Field of Classification Search
None
See application file for complete search history.

(56) References Cited

U.S. PATENT DOCUMENTS

| 5,472,881 | A  | 12/1995 | Beebe et al. |
| 6,361,944 | B1 | 3/2002  | Mirkin et al. |
| 6,417,340 | B1 | 7/2002  | Mirkin et al. |
| 6,495,324 | B1 | 12/2002 | Mirkin et al. |
| 6,506,564 | B1 | 1/2003  | Mirkin et al. |
| 6,582,921 | B2 | 6/2003  | Mirkin et al. |
| 6,610,491 | B2 | 8/2003  | Mirkin et al. |
| 6,635,311 | B1 | 10/2003 | Mirkin et al. |
| 6,645,721 | B2 | 11/2003 | Mirkin et al. |
| 6,673,548 | B2 | 1/2004  | Mirkin et al. |
| 6,677,122 | B2 | 1/2004  | Mirkin et al. |

(Continued)

FOREIGN PATENT DOCUMENTS

WO    WO-2005/003394    1/2005

OTHER PUBLICATIONS

Caruntu et al "Attachment of gold nanograins onto colloidal magnetite nanocrystals" Chem. Mater. May 20, 2005, 17: 3398-3402.*

(Continued)

*Primary Examiner* — Betty Forman
(74) *Attorney, Agent, or Firm* — Marshall, Gerstein & Borun LLP

(57) ABSTRACT

Composite particles and methods of synthesizing a composite particle are disclosed, in particular, methods of synthesizing a composite particle comprising a dielectric component, a magnetic component, and a gold shell are disclosed. Further disclosed herein are methods of detecting a target compound using the composite particles of the present invention. Also disclosed are photonic crystals that can be manipulated with an external magnetic field comprising the composite particles of the present invention.

11 Claims, 9 Drawing Sheets

(56) References Cited

U.S. PATENT DOCUMENTS

| | | | |
|---|---|---|---|
| 6,682,895 | B2 | 1/2004 | Mirkin et al. |
| 6,709,825 | B2 | 3/2004 | Mirkin et al. |
| 6,720,147 | B2 | 4/2004 | Mirkin et al. |
| 6,720,411 | B2 | 4/2004 | Mirkin et al. |
| 6,726,847 | B2 | 4/2004 | Mirkin et al. |
| 6,730,269 | B2 | 5/2004 | Mirkin et al. |
| 6,740,491 | B2 | 5/2004 | Mirkin et al. |
| 6,750,016 | B2 | 6/2004 | Mirkin et al. |
| 6,759,199 | B2 | 7/2004 | Mirkin et al. |
| 6,767,702 | B2 | 7/2004 | Mirkin et al. |
| 6,773,823 | B2 * | 8/2004 | O'Connor et al. ............ 428/548 |
| 6,773,884 | B2 | 8/2004 | Mirkin et al. |
| 6,777,186 | B2 | 8/2004 | Mirkin et al. |
| 6,812,334 | B1 | 11/2004 | Mirkin et al. |
| 6,818,753 | B2 | 11/2004 | Mirkin et al. |
| 6,827,979 | B2 | 12/2004 | Mirkin et al. |
| 6,828,432 | B2 | 12/2004 | Mirkin et al. |
| 6,861,221 | B2 | 3/2005 | Mirkin et al. |
| 6,878,814 | B2 | 4/2005 | Mirkin et al. |
| 6,902,895 | B2 | 6/2005 | Mirkin et al. |
| 6,903,207 | B2 | 6/2005 | Mirkin et al. |
| 6,962,786 | B2 | 11/2005 | Mirkin et al. |
| 6,969,761 | B2 | 11/2005 | Mirkin et al. |
| 6,974,669 | B2 | 12/2005 | Mirkin et al. |
| 6,984,491 | B2 | 1/2006 | Mirkin et al. |
| 6,986,989 | B2 | 1/2006 | Mirkin et al. |
| 2002/0132045 | A1 | 9/2002 | Halas et al. |
| 2004/0219361 | A1 | 11/2004 | Cui et al. |
| 2005/0277205 | A1 | 12/2005 | Lee et al. |
| 2006/0105170 | A1 * | 5/2006 | Dobson et al. ................ 428/403 |
| 2006/0148104 | A1 * | 7/2006 | Marini et al. ................. 436/524 |

OTHER PUBLICATIONS

Allara et al., *Colloid Interface Sci.*, The study of the gas-solid interaction of acetic acid with a cuprous oxide surface using reflection-absorption spectroscopy, 49:410-421 (1974).

Allara et al., "Spontaneously Organized Molecular Assemblies. 1. Formation, Dynamics, and Physical Properties of n-Alkanoic Acids Adsorbed from Solution on an Oxidized Aluminum Surface," *Langmuir*, 1:45-52 (1985).

Burwell, *Chemical Technology*, "Modified silica gels as adsorbents and catalysts", 4:370-377 (1974).

Caruso, "Nanoengineering of Particle Surfaces," *Adv. Mat.*, 13:11-22 (2001).

Duff et al., "A New Hydrosol of Gold Clusters. 2. A Comparison of Some Different Measurement Techniques," *Langmuir*, 9:2301-2317 (1993).

Eckstein, Oligonucleotides and Analogues, "Modern machine-aided methods of oligodeoxyribonucleotide synthesis", 1st Ed. (Oxford University Press, New York, 1991) pp. 1-24.

Eltekova et al., "Adsorption of Aromatic Compounds from Solutions on Titanium Dioxide and Silica," *Langmuir*, 3:951-957 (1987).

Gates et al, "Photonic Crystals than can be Addressed with an External Magnetic Field," *Adv. Mater.*, 13(21):1605-1608 (2001).

Grabar et al., "Prepartation and Characterization of Au Colloid Monolayers," *Anal. Chem.*, 67:735-743, 1995.

Graf et al., "A General Method to Coat Colloidal Particles with Silica," *Langmuir*, 19:6693-6700 (2003).

Hickman et al., "Combining Spontaneous Molecular Assembly with Microfabrication to Pattern Surfaces: Selective Binding of Isonitriles to Platinum Microwires and Characterization by Electrochemistry and Surfaces Spectroscopy," *J. Am.Chem. Soc.*, 111:7271-7272 (1989).

Hubbard, "Electrochemistry of Well-Defined Surfaces," *Acc. Chem. Res.*, 13:177-184 (1980).

Iler, *The Chemistry of Silica*, Chapter 6, (Wiley 1979) pp. 624-633.

Jin et al., "What Controls the Melting Properties of DNA-Linked Gold Nanoparticle Assemblies?" *Chem. Soc.*, 125:1643-1654 (2003).

Lee et al., "Adsorption of Ordered Zirconium Phosphonate Multilayer Films on Silicon and Gold Surfaces," *Phys. Chem.*, 92:2597-2601 (1988).

Maoz et al., "Penetration-Controlled Reactions in Organized Monolayer Assemblies. 2. Aqueous Permanganate Interaction with Self-Assembling Monolayers of Long-Chain Surfactants," *Langmuir*, 3:1045-1051 (1987).

Matteucci et al., "Synthesis of Deoxyoligonucleotides on a Polymer Support," *J. Am. Chem. Soc.*, 103:3185-3191 (1981).

Mucic et al., "Synthesis and Characterizations of DNA with Ferrocenyl Groups Attached to Their 5'-Termini : Electrochemical Characterization of a Redox-Active Nucleotide Monolayer," *Chem. Comm.*, 555-557 (1996).

Nuzzo et al., "Spontaneously Organized Molecular Assemblies. 3. Preparation and Properties of Solution Adsorbed Monolayers of Organic Disulfides on Gold Surfaces," *J. Am. Chem. Soc.*, 109:2358-2368 (1987).

Pham et al., "Preparation and Characterization of Gold Nanoshells Coated with Self-Assembled Monolayers," *Langmuir*, 18:4915-4920 (2002).

Philipse et al., "Magnetic Silica Dispersions: Preparation and Stability of Surface-Modified Silica Particles with a Magnetic Core," *Langmuir*, 10:92-99 (1994).

Soriaga et al., "Determination of the Orientation of Aromatic Molecules Adsorbed on Platinum Electrodes.[1,2] The Effect of Solute Concentration," *Chem. Soc.*, 104:3937-3945 (1982).

Spasova et al., "Magnetic and optical tunable microspheres with a magnetite/gold nanoparticle shell," *J. of Mat. Chem.*, 15:2095-2098 (2005).

Stoeva et al., "Three-Layer Composite Magnetic Nanoparticle Probes for DNA," *J Am. Chem. Soc.*, 127:15362-15363 (2005).

Subramanian et al., "Ordered Macroporous Materials by Colloidal Assembly: A Possible Route to Photonic Bandgap Materials," *Adv. Mater.*, 11(15):1261-1265 (1999).

Sun et al., "Monodisperse $MFe_2O_4$(M=Fe, Co, Mn) Nanoparticles," *Chem. Soc.*, 126:273-279 (2004).

Timmons et al., "Investigation of Fatty Acid Monolayers on Metals by Contact Potential Measurements," *Phys. Chem.*, 69:984-990 (1965).

Wasserman et al., "Structure and Reactivity of Alkylsiloxane Monolayers Formed by Reaction of Alkytrichlorosilanes on Silicon Substrates," *Langmuir*, 5:1074-1087 (1989).

Whitesides, Proceedings of the Robert A. Welch Foundation 39th Conference on Chemical Research Nanophase Chemistry, Houston, Tex., pp. 109-121 (1995).

International Search Report for International Application No. PCT/US2006/031118, dated Mar. 20, 2008.

Written Opinion for International Application No. PCT/US2006/031118, dated Mar. 20, 2008.

Ge et al., "Highly Tunable Superparamagnetic Colloidal Photonic Crystals," *Angew. Chem. Int. Ed.*, 46:7428-7431 (2007).

* cited by examiner

COMPOSITE PARTICLES

CROSS-REFERENCE TO RELATED APPLICATIONS

This application claims the benefit of U.S. Provisional Application Ser. No. 60/707,128 filed Aug. 10, 2005.

STATEMENT OF GOVERNMENTAL INTERESTS

This invention was made with government support under Air Force Office of Scientific Research (AFOSR) grant No. F49620-01-1-0401, National Science Foundation (NSF-NSEC) grant No. EEC-011-8025, Homeland Security Advanced Research Projects Agency (HSARPA) grant No. W81XWH-05-2-0036, and National Institutes of Health (NIH) grant No. 1DP1 0D000285-01. The government has certain rights in this invention.

FIELD OF THE INVENTION

The present invention relates to a method of synthesizing a composite particle, comprising a dielectric component, a magnetic component, and a gold shell. More particularly, the present invention relates to methods of synthesizing composite particles and methods of using the disclosed particles in biological diagnoses and/or detection and as building blocks of photonic crystals.

BACKGROUND OF THE INVENTION

Gold nanoparticles functionalized with oligonucleotides are important reagents in many highly sensitive and selective oligonucleotide and protein detection schemes. They are also key building blocks in several assembly schemes that utilize the chemically programmable, sequence specific hybridization properties of nucleic acids. The use of gold particles in biodetection stems from the existence of well established and straightforward methods for the functionalization of a gold surface with ligands containing thiol or disulfide groups, the cooperative binding properties of the probes, their intense optical properties, and their catalytic properties. Each of these properties leads to a selectivity or sensitivity advantage over conventional probes.

Magnetic particles also have been widely used in diagnostic and therapeutic applications. Although methods of synthesizing magnetic particles with control over size and shape exist, surface functionalization of magnetic particles with biomolecules often requires elaborate synthetic schemes.

There exists a need for synthetic methods that provide composite materials having both the stability, surface chemistry, and optical properties of gold particles and the magnetic properties of superparamagnetic particles. Core-shell approaches to realizing such probe structures have met with limited success. Direct coating of magnetic particles with gold is a difficult task due to the dissimilar nature of the two surfaces. Methods based on the synthesis of one of the compositions in the presence of the other have led to structures with minimal interface contact between gold and the magnetic particles.

SUMMARY

The present invention relates to a method of forming composite particles. In particular, the present invention provides a method of forming composite particles comprising a dielectric component, magnetic component, and gold shell.

Another aspect of the present invention provides components for the preparation of photonic crystals comprising the composite particles disclosed herein. Due to the magnetic properties of the composite particles, the photonic crystals can be manipulated by applied magnetic fields.

Another aspect of the present invention is to provide a method of using the composite particles of the present invention in identifying target compounds. The methods comprise interacting a target compound with a surface-modified composite particle, wherein the surface is modified with a moiety capable of interacting selectively with the target compound, and this interaction is detectable.

Another aspect of the present invention is to provide a method of using the composite particles of the present invention in the separation of a target compound from a mixture. The methods comprise interacting a mixture containing the target compound with a surface-modified composite particle, wherein the surface is modified with a moiety capable of binding selectively to the target compound, applying a magnetic field to cause the separation of the target compound bound to the surface-modified composite particle from the mixture and, optionally, treating the target compound bound to the surface-modified composite particle with an agent that causes the target compound to be released from the surface-modified composite particle.

Another aspect of the invention provides methods detecting a target compound in a mixture comprising the steps of contacting the target with one or more surface modified composite particles of the invention, wherein the surface is modified with a moiety capable of binding selectively to the target compound, and one or more detectable probes under conditions in which the composite particle(s) and the detectable probe(s) bind to the target to form an aggregate, isolating the aggregate by applying a magnetic field to the mixture, and detecting the detectable probe(s). Methods optionally comprise a step of treating the aggregate to separate the target compound from the detectable probe, the composite particle or both

DETAILED DESCRIPTION OF THE PREFERRED EMBODIMENTS

The present invention is directed to a synthetic procedure that provides composite particles, which comprise a dielectric component, a magnetic component, and a gold component.

Figure 1:
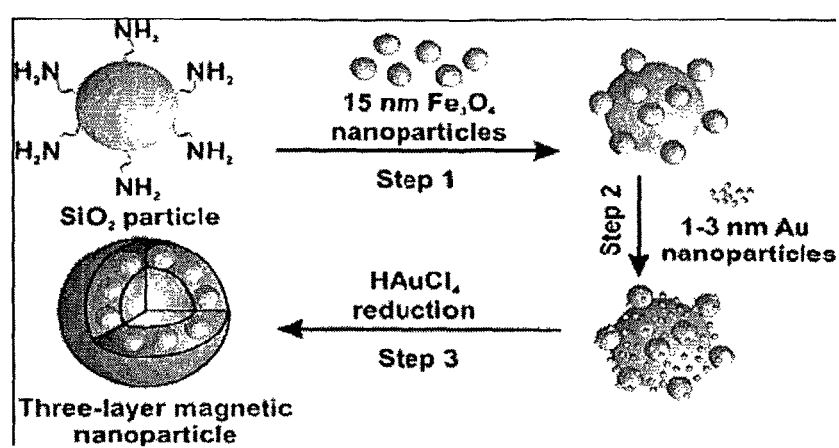
FIG. 1 is a schematic showing the synthesis of composite particles of the present invention.

The method of the present invention comprises a three step process for forming composite particles. More particularly, the method of the present invention comprises (a) admixing a dielectric component and a magnetic component to form a first intermediate, (b) admixing the first intermediate and gold seed to form a second intermediate, and (c) forming a gold shell on the second intermediate by admixing the second intermediate with a gold source and a reducing agent to form a composite particles of the present invention. This method is depicted in the schematic of FIG. 1.

As used herein, "composite particle" refers to a particle of about 60 to about 5000 nm diameter and comprising a dielectric component, a magnetic component, and a gold shell. Composite particles having a diameter less than about 60 nm exhibit weak magnetic properties, while composite particles having a diameter greater than about 5000 nm are more prone to aggregation. A preferred diameter is about 100 to about 600 nm, more preferably about 110 to about 300 nm, and most preferably about 125 nm to about 275 nm. The composite particles disclosed herein exhibit superparamagnetic and/or ferromagnetic properties and have a gold shell that can be functionalized using procedures known in the art, such as, e.g., modified with thiol containing molecules.

As used herein, "dielectric component" refers to a particle comprising a substance that is highly resistant to the flow of electric current. Examples of dielectric components include, but are not limited to inorganic oxides, such as $SiO_2$ (silica), $Nb_2O_5$, $Cr_2O_3$, $ZrO_2$, $ZnO$, $CdO$, $CeO_2$, $WO_3$, $Al_2O_3$, $TiO_2$ (titania), and the like. The dielectric component optionally can be modified, for example, amino-modified, thiol-modified, carboxyl-modified, streptavidin-modified, or biotin-modified, or the surface may be modified with natural or synthetic polymers such as polystyrene and poly(methyl methacrylate). Preferred dielectric components are ones exhibiting a positive Zeta potential. A preferred dielectric component is amino-modified silica.

The dielectric component can have a thickness or lateral dimension such as a diameter of about 50 to about 4500 nm, more preferably about 150 to about 250 nm, most preferably about 175 to about 225 nm. Also contemplated are thicknesses of the dielectric component of about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 500, about 1000, about 1500, about 2000, about 2500, about 3000, about 3500, about 4000, and about 4200 nm. In various embodiments, the dielectric component has a thickness tailored to exhibit desired photonic crystal properties. Such thicknesses can be readily determined by one of skill in the art, in view of the disclosure herein and the examples provided below.

As used herein, the term "thickness" is interchangeably referred to as diameter. Because the composite particles comprise more than one component, each component has a certain thickness that contributes to the overall diameter of the composite particle.

The dielectric component can have a $\zeta$-potential of about +25 to about +75 millivolts (mV), more preferably about +40 to about +60 mV, and most preferably about +45 to about +55 mV. Also contemplated is a dielectric component having a $\zeta$-potential of about +26, about +27, about +28, about +29, about +30, about +31, about +32, about +33, about +34, about +35, about +36, about +37, about +38, about +39, about +40, about +41, about +42, about +43, about +44, about +45, about +45, about +46, about +47, about +48, about +49, about +50, about +51, about +52, about +53, about +54, about +55, about +56, about +57, about +58, and about +59 mV.

As used herein, "magnetic component" refers to a particle comprising a substance exhibiting ferromagnetic, ferrimagnetic, and/or superparamagnetic properties, when present in the amounts disclosed herein. The magnetic component can comprise iron, nickel, cobalt, neodymium, and/or their alloys, other alloys that exhibit ferromagnetic, ferrimagnetic, and/or superparamagnetic properties, ferrites having a formula $M^*Fe_2O_4$, wherein $M^*$ is a divalent cation such as, for example, $Mn^{2+}$, $Mg^{2+}$, or $Co^{2+}$. One suitable material for the magnetic component is an iron oxide, such as maghemite, or more preferably, magnetite. Also suitable magnetic components include an alloy or a mixture of elemental materials. Specific examples of magnetic components include, but are not limited to, $Fe_3O_4$, $Fe_3O_4$, FePt, $CoFe_2O_4$ or particles thereof with modified surfaces. The magnetic component optionally can be modified, or primed, for example, with silica. Preferred dielectric components are ones exhibiting a negative Zeta potential. A preferred magnetic component is silica-primed $Fe_3O_4$. Other coatings contemplated include titania, polymers (e.g., polystyrene, poly(vinylpyrrolidone), poly(methyl methacrylate)), and combinations of poly(vinylpyrrolidone) and silica (see Graf et al., *Langmuir*, 19:6693-6700 (2003) and Caruso, *Adv. Mat.*, 13:11-22 (2001).

The particles of the magnetic component can have a thickness of about 2 to about 50 nm, more preferably about 10 to about 30 nm, and most preferably about 12 to about 16 nm. Also contemplated are magnetic components having a thickness of about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, and about 59 nm.

The magnetic component can have a $\zeta$-potential from about −10 to about −60 mV, more preferably about −25 to about −45 mV, and most preferably about −30 to about −40 mV. Also contemplated are magnetic components having a $\zeta$-potential of about −11, about −12, about −13, about −14, about −15, about −16, about −17, about −18, about −19, about −20, about −21, about −22, about −23, about −24, about −25, about −26, about −27, about −28, about −29, about −30, about −31, about −32, about −33, about −34, about −35, about −36, about −37, about −38, about −39, about −40, about −41, about −42, about −43, about −44, about −45, about −46, about −47, about −48, about −49, about −50, about −51, about −52, about −53, about −54, about −55, about −56, about −57, about −58, and about −59 mV.

The dielectric component and the magnetic component can be admixed to form a first intermediate. The first intermediate can have the dielectric component and magnetic components present in a component/component ratio of about 1:200 to about 1:2000, preferably about 1:300 to about 1:1500, and more preferably about 1:500 to about 1:1200 particles/particles. This ratio can also be expressed as mg/mg and is typically about 15:1 to about 1.5:1, preferably about 10:1 to about 2:1, and more preferably about 6:1 to about 2.5:1. The dielectric and magnetic components are mixed for a length of time sufficient to allow binding and/or admixture of the components. Typically, the length of time is about 15 to about 45 minutes (min), more preferably about 20 to about 40 min, and most preferably about 25 to about 35 min.

As used herein, "first intermediate" refers to a particle resulting from an admixture of the dielectric component and the magnetic component. It is theorized, but not relied upon herein, that the first intermediate is formed by electrostatic interactions between the dielectric component and the magnetic component.

The first intermediate can comprise a $SiO_2$—$Fe_3O_4$ particle or any combination of dielectric components as disclosed above with magnetic components as described above.

The first intermediate is isolated, preferably, by centrifugation or sedimentation wherein said isolation is performed in a manner such as is known in the art, for example centrifugation using a rotor having a diameter of 12 centimeters. The mixture containing the first intermediate typically is centrifuged at about 1000 to about 3000 revolutions per minute (rpm), preferably about 1500 to about 2500 rpm, and more preferably about 1750 to about 2250 rpm. The first intermediate typically is centrifuged for about 2 to about 10 min, preferably about 4 to about 8 min, and more preferably about 5 to about 6 min. The first intermediate also can be redispersed in a suitable carrier and recentrifuged 1 to about 5 times, preferably about 2 to about 4 times, more preferably 2 times.

The first intermediate can be redispersed in a suitable carrier, typically water. Other suitable carriers include, but are not limited to, alcohols, ethers, dimethylsulfoxide, dimethylformamide, and the like.

After redispersing the first intermediate in a suitable carrier, gold seeds can be added. The first intermediate and gold seeds are admixed to form a second intermediate. The first intermediate and gold seeds can be admixed for about 15 to about 45 min, preferably about 20 to 40 min, and more preferably about 25 to about 35 min. The gold seeds are admixed with the first intermediate to provide a surface on which gold can be attached. The second intermediate can be prepared from an admixture of a first intermediate and gold seeds in a (particle/particle) ratio from about 1:5000 to about 1:50,000, preferably about 1:7000 to about 1:25,000, and more preferably about 1:10,000 to about 1:20,000 particle/particle. This ratio can also be expressed as mg/mg, and is typically about 15:1 to about 1.5:1, preferably about 10.7:1 to about 3:1, and more preferably about 7.5:1 to about 3.75:1.

As used herein, "second intermediate" refers to the particles resulting from a combination of the first intermediate with gold seeds. In a preferred embodiment of the present invention, the second intermediate comprises $SiO_2$—$Fe_3O_4$—$Au_{seeds}$ particles.

As used herein, "gold seed" refers to gold nanoparticles having a size of about 1 to about 20 nm, preferably about 1 to about 10 nm, and more preferably about 1 to about 3 nm. The gold seeds can be prepared according to known procedures, such as those reported in, e.g., Duff et al., *Langmuir* 9:2301 (1993). In a specific embodiment, gold seeds were synthesized by reduction of chlorauric acid ($HAuCl_4 \cdot 3H_2O$) with tetrakis(hydroxymethyl)phosphonium chloride (THPC) to form gold seeds having a diameter about 3 nm.

The second intermediate can be isolated by centrifuging or sedimentation as disclosed above, for example, at about 2000 to about 8000 rpm, preferably about 3000 to about 6000 rpm, and more preferably about 4500 to about 5500 rpm, for about 2 to about 10 min, preferably about 4 to about 8 min, and more preferably about 5 to about 6 min. The second intermediate can be centrifuged 1 to about 10 times, preferably about 2 to about 8 times, and more preferably about 4 to about 7 times. The number of times the second intermediate is centrifuged is dependent upon the desired purity of the second intermediate prior to performing the next step of the disclosed method.

The second intermediate can be redispersed in a suitable carrier, typically water, prior to reaction with a gold source and a reducing agent. Other suitable carriers include, but are not limited to, alcohols, ethers, dimethylsulfoxide, and dimethylformamide. The amount of carrier will depend upon the scale of the preparation of composite particles, but for an about 1 to about 100 mg scale preparation, the amount of carrier is typically about 0.5 to about 30 mL, preferably about 3 to about 15 mL, and more preferably about 5 to about 8 mL.

A gold shell can be formed by admixing the second intermediate, a gold source, and a reducing agent, which results in the composite particle of the present invention. As used herein used, "gold shell" refers to a layer formed on the surface of the second intermediate by the reduction of a gold source. Without intending to be bound by any theory, it is postulated that the gold seeds of the second intermediate serve as nucleation sites for the growth of the gold shell.

Examples of a gold source for preparation of the gold shell include, but are not limited to, $HAuCl_4$, $AuCl_3$, gold acetate $(Au(CH_3COO)_3)$, $KAu(CN)_4$, $KAu(CN)_2$. Examples of reducing agents include, but are not limited to, formaldehyde, sodium borohydride, hydrazine, ascorbic acid, citric acid, glucose, hydroxylamine, and tetrakis(hydroxymethyl)phosphonium chloride (THPC). In various embodiments, the gold source is added prior to the reducing agent, while in other embodiments, the reducing agent is added prior to the gold source.

The second intermediate, gold source, and reducing agent can be admixed for about 30 to about 60 min, preferably about 35 to about 55 min, and more preferably about 40 to about 50 min.

The color of the admixture of the second intermediate, gold source, and reducing agent changes from colorless to purple to blue to red over time, which indicates that the particles are being altered. A blue color corresponds to the formation of a gold shell, and a red color corresponds to the formation of free gold particles. This color change can be used to monitor the progress of the reaction.

The thickness of the gold shell can be tailored to desired end properties by manipulation of the amount of gold source and/or reducing agent. The thickness can be about 5 to about 100 nm. The gold shell has a thickness preferably of less than about 50 nm. Also contemplated are gold shell thicknesses of about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, and about 99 nm.

The resulting composite particle can be isolated by centrifuging or sedimentation as disclosed above, the admixture of second intermediate, gold source, and reducing agent for about 1 to about 5 min, preferably about 2 to about 4 min, and more preferably about 2.5 to about 3.5 min, at about 1500 to about 3500 rpm, preferably about 2000 to about 3000 rpm, and more preferably about 2250 to about 2750 rpm. Centrifuging can be performed 1 to about 10 times, preferably about 4 to about 6 times, and more preferably about 5 to about 6 times.

A composite particle produced by the method of the present invention comprises a dielectric component, magnetic component, and gold shell. The composite particle can have a dielectric component forming an innermost core, a magnetic component adjacent the dielectric component, and a gold shell adjacent to and forming an outermost covering over the magnetic component. Alternatively, a magnetic component can form an innermost core, and a dielectric component can be adjacent to the magnetic component, with a gold shell forming an outermost covering.

Also disclosed herein are photonic crystals comprising the composite particles. As used herein, "photonic crystal" refers to a substance with a periodic three dimensional (3D) structure composed of spatially ordered building units and a photonic band structure that can exclude the propagation of the photons within a specific range of frequencies inside the crystal. Photonic crystals can be formed by self-assembly into a crystalline array of at least two composite particles produced from the method of the present invention. The photonic crystals produced in such way can be manipulated with an external magnetic field.

As used herein, the term "manipulate," when used in relation to photonic crystals, refers to changing the spatial position and orientation of the magnetic photonic crystal using an external force, including, but not limited to, a magnetic field.

A photonic crystal can be formed via self-assembly of two or more composite particles. In various embodiments, the photonic crystal comprises composite particles having the same properties, such as types and strength of magnetism of the magnetic components, and thicknesses of dielectric components and gold shells, while in other embodiments, the photonic crystals comprise composite particles having different properties. Regardless of the composition of the photonic crystals disclosed herein, they can be manipulated with an external magnetic field.

Further disclosed herein is a method of identifying a target compound comprising contacting a sample containing or suspected of containing a target compound with an surface-modified composite particle of the present invention, wherein the surface is specific for the target compound. The composite particle can be modified with a wide variety of moieties, such as, for example, oligonucleotides, antigens, antibodies, polymers, polypeptides, polysaccharides, and the like. Methods for modifying a gold surface to attach such moieties are known in the art, e.g., in U.S. Patent Publications 2006/ 0051798; 2006/0040286; 2005/0037397; 2004/0131843; 2004/0110220; 2004/0086897; 2004/0072231; 2004/ 0038255; 2003/0207296; 2003/0180783; 2003/0148282; 2003/0143538; 2003/0129608; 2003/0124528; 2003/ 0113740; 2003/0087242; 2003/0068622; 2003/0059777; 2003/0054358; 2003/0049631; 2003/0049630; 2003/ 0044805; 2003/0022169; 2002/0192687; 2002/0182613; 2002/0182611; 2002/0177143; 2002/0172953; 2002/ 0164605; 2002/0160381; 2002/0155462; 2002/0155461; 2002/0155459; 2002/0155458; 2002/0155442; 2002/ 0146720; 2002/0137072; 2002/0137071; 2002/0137070; 2002/0137058; 2002/0127574; each of which is incorporated herein in its entirety by reference. The choice of moiety to modify the surface of the composite particle will depend upon the target compound, and such choice can be easily made by one of skill in the art. For example, for detection of an oligonucleotide target compound, the surface of the composite particle can be modified with a complementary oligonucleotide, and for detection of an antigen, the surface of the composite particle can be modified with an appropriate antibodies. Conversely, for the detection of an antigen, the surface can be modified with an appropriate antibody.

As used herein, the term "target compound" refers to a compound of interest which is detectable using surface-modified composite particles. Typically, the target compound is an oligonucleotide, but can be any compound [of interest] which is detectable by a surface-modified composite particle. Non-limiting examples of target compounds include oligonucleotides, antigens, antibodies, polypeptides, polymers, ionic compounds, metals, metal ions, and ligands.

In various embodiments, the target compound comprises at least two portions. The lengths of these portions and the distance(s), if any, between them are chosen so that when the surface-modified composite particles interact with the target compound a detectable change occurs. These lengths and distances can be determined empirically and will depend on the type of particle used and its size and the type of electrolyte which will be present in solutions used in the assay. Also, when a target compound is to be detected in the presence of other oligonucleotides, the portions of the target to which the oligonucleotide(s) on oligonucleotide-modified composite particle is to bind must be chosen so that they contain a sufficiently unique sequence such that detection of the nucleic acid will be specific. These techniques are well known in the art and can be found, for example, in U.S. Pat. Nos. 6,986, 989; 6,984,491; 6,974,669; 6,969,761; 6,962,786; 6,903,207; 6,902,895; 6,878,814; 6,861,221; 6,828,432; 6,827,979; 6,818,753; 6,812,334; 6,777,186; 6,773,884; 6,767,702; 6,759,199; 6,750,016; 6,740,491; 6,730,269; 6,726,847; 6,720,411; 6,720,147; 6,709,825; 6,682,895; 6,677,122; 6,673,548; 6,645,721; 6,635,311; 6,610,491; 6,582,921; 6,506,564; 6,495,324; 6,417,340; and 6,361,944, each of which is herein incorporated by reference in its entirety.

In embodiments where the target compound comprises an oligonucleotide, the detectable change that occurs upon hybridization of a target compound on an oligonucleotide-modified composite particle to the target can be a color change, formation of aggregates of the oligonucleotide-modified composite particles, and/or a precipitation of the aggregated oligonucleotide-modified composite particles. The color changes can be observed with the naked eye or spectroscopically. The formation of aggregates of the oligonucleotide-modified composite particles can be observed by electron microscopy by nephelometry, or the eye. The precipitation of the aggregated oligonucleotide-modified composite particles can be observed with the naked eye or microscopically. Preferred are changes observable with the naked eye. Particularly preferred is a color change observable with the naked eye.

In certain embodiments, the target compound can be detected due to its association with the surface-modified composite particle. Since the composite particle is magnetic, the complex of target compound and composite particle can be removed from a solution by application of a magnetic field. The target compound can be disassociated from the composite particle and detected using analytic techniques such as, for example, liquid chromatography, gas chromatography, mass spectrometry, gel electrophoresis, capillary electrophoresis, nuclear magnetic resonance, PCR, and the like.

Examples of the uses of the method for identifying a target compound include but are not limited to, the diagnosis and/or monitoring of viral diseases (e.g., human immunodeficiency virus, hepatitis viruses, herpes viruses, cytomegalovirus, and Epstein-Barr virus), bacterial diseases (e.g., tuberculosis, Lyme disease, *H. pylori, Escherichia coli* infections, *Legionella* infections, *Mycoplasma* infections, *Salmonella* infections), sexually transmitted diseases (e.g., gonorrhea), inherited disorders (e.g., cystic fibrosis, Duchene muscular dystrophy, phenylketonuria, sickle cell anemia), and cancers (e.g., genes associated with the development of cancer); in forensics; in DNA sequencing; for paternity testing; for cell line authentication; for monitoring gene therapy; and for many other purposes.

In various embodiments, the detection of a target compound is used in conjunction with drug discovery or DNA or oligonucleotide interacting compounds (e.g., intercalators and binders). A target compound can be assessed for its ability to specifically bind to a known oligonucleotide, which is bound to the surface of a composite particle disclosed herein. The target compounds that bind or interact can be identified and isolated by applying a magnetic field. Upon disassociation from the composite particle, the target compound can be analyzed using common analytic techniques.

As used herein, the term "oligonucleotide" refers to a single-stranded oligonucleotide of 200 or less nucleobases. Methods of making oligonucleotides of a predetermined sequence are well-known. See, e.g., Sambrook et al., *Molecular Cloning: A Laboratory Manual* (2nd ed. 1989) and F. Eckstein (ed.) *Oligonucleotides and Analogues*, 1st Ed. (Oxford University Press, New York, 1991). Solid-phase synthesis methods are preferred for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically.

In various aspects, the oligonucleotide which modified the surface of a composite particle disclosed herein is about 5 to about 100 nucleotides in length, about 5 to about 90 nucleotides in length. about 5 to about 80 nucleotides in length, about 5 to about 70 nucleotides in length, about 5 to about 60 nucleotides in length, about 5 to about 50 nucleotides in length, about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, or about 5 to about 10 nucleotides in length. Methods are provided wherein the oligonucleotide is a DNA oligonucleotide, an RNA oligonucleotide, or a modified form of either a DNA oligonucleotide or an RNA oligonucleotide.

In various aspects, the methods include use of an oligonucleotide which is 100% complementary to the target oligonucleotide, i.e., a perfect match, while in other aspects, the oligonucleotide is at least (meaning greater than or equal to) about 95% complementary to the target compound over the length of the oligonucleotide, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20% complementary to the target compound over the length of the oligonucleotide to the extent that the oligonucleotide is able to achieve the desired degree of inhibition of a target gene product.

Examples of one class of target compounds that can be detected by the method of the present invention includes but is not limited to genes (e.g., a gene associated with a particular disease), viral RNA and DNA, bacterial DNA, fungal DNA, cDNA, mRNA, RNA and DNA fragments, oligonucleotides, synthetic oligonucleotides, modified oligonucleotides, single-stranded and double-stranded nucleic acids, natural and synthetic nucleic acids, and the like. The target compound may be isolated by known methods, or may be detected directly in cells, tissue samples, biological fluids (e.g., saliva, urine, blood, serum), solutions containing PCR components, solutions containing large excesses of oligonucleotides or high molecular weight DNA, and other samples, as also known in the art. 15 See, e.g., Sambrook et al., *Molecular Cloning: A Laboratory Manual* (2nd ed. 1989) and B. D. Hames and S. J. Higgins, Eds., *Gene Probes* 1 (IRL Press, New York, 1995). [corresponding paragraphs are needed for protein and other non-NA targets—see 24003 and the other bio-barcode applications]

In other aspects, the target compound is a member of a specific binding pair which comprise nucleic acid, oligonucleotide, peptide nucleic acid, polypeptide, antibody, antigen, carbohydrate, protein, peptide, amino acid, hormone, steroid, vitamin, drug, virus, polysaccharides, lipids, lipopolysaccharides, glycoproteins, lipoproteins, nucleoproteins, oligonucleotides, antibodies, immunoglobulins, albumin, hemoglobin, coagulation factors, peptide and protein hormones, non-peptide hormones, interleukins, interferon, cytokines, peptides comprising a tumor-specific epitope, cells, cell-surface molecules, microorganisms, fragments, portions, components or products of microorganisms, small organic molecules, nucleic acids and oligonucleotides, metabolites of or antibodies to any of the above substances.

As used herein "oligonucleotide-modified composite particle" refers to the composite particle of the present invention with one or more oligonucleotides, or modified form thereof, which is from about 5 to about 100 nucleotides in length, attached thereto. Methods are also contemplated wherein the oligonucleotide is about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, and all oligonucleotides intermediate in length of the sizes specifically disclosed to the extent that the oligonucleotide is able to achieve the desired result. Accordingly, oligonucleotides of about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, and about 100 nucleotides in length are contemplated. (What is the difference between 63 and 66?)

In various aspects of the method, a plurality of oligonucleotides may be attached to the composite particle. As a result, each oligonucleotide-modified composite particle can have the ability to bind to a plurality of target compounds. In various aspects of the method the plurality of oligonucleotides may be identical. Methods are also contemplated wherein the plurality of oligonucleotides includes about 10 to about 100,000 oligonucleotides, about 10 to about 90,000 oligonucleotides, about 10 to about 80,000 oligonucleotides, about 10 to about 70,000 oligonucleotides, about 10 to about 60,000 oligonucleotides, 10 to about 50,000 oligonucleotides, 10 to about 40,000 oligonucleotides, about 10 to about 30,000 oligonucleotides, about 10 to about 20,000 oligonucleotides, about 10 to about 10,000 oligonucleotides, and all numbers of oligonucleotides intermediate to those specifically disclosed to the extent that the oligonucleotide-modified composite particle is able to achieve the desired result.

In various aspects of the methods, at least one oligonucleotide is bound to the composite particle through a 5' linkage and/or the oligonucleotide is bound to the composite particle through a 3' linkage. In various aspects, at least one oligonucleotide is bound through a spacer to the composite particle. In these aspects, the spacer is an organic moiety, a polymer, a water-soluble polymer, a nucleic acid, a polypeptide, and/or an oligosaccharide. Methods of functionalizing the oligonucleotides to attach to a surface of a nanoparticle are well known in the art. See Whitesides, *Proceedings of the Robert A. Welch Foundation 39th Conference On Chemical Research Nanophase Chemistry*, Houston, Tex., pages 109-121 (1995). See also, Mucic et al. *Chem. Comm.* 555-557 (1996) (describes a method of attaching 3' thiol DNA to flat gold surfaces; this method can be used to attach oligonucleotides to nanoparticles). The alkanethiol method can also be used to attach oligonucleotides to other metal, semiconductor and magnetic colloids and to the other nanoparticles listed above. Other functional groups for attaching oligonucleotides to solid surfaces include phosphorothioate groups (see, e.g., U.S. Pat. No. 5,472,881 for the binding of oligonucleotide-phosphorothioates to gold surfaces), substituted alkylsiloxanes (see, e.g. Burwell, *Chemical Technology*, 4:370-377 (1974) and Matteucci and Caruthers, *J. Am. Chem. Soc.*, 103:3185-3191 (1981) for binding of oligonucleotides to silica and glass surfaces, and Grabaretal., *Anal. Chem.*, 67:735-743 for binding of aminoalkylsiloxanes and for similar binding of mercaptoaklylsiloxanes). Oligonucleotides terminated with a 5' thionucleoside or a 3' thionucleoside may also be used for attaching oligonucleotides to solid surfaces. The following references describe other methods which may be employed to attached oligonucleotides to nanoparticles: Nuzzo et al., *J. Am. Chem. Soc.*, 109:2358 (1987) (disulfides on gold); Allara and Nuzzo, Langmuir, 1:45 (1985) (carboxylic acids on aluminum); Allara and Tompkins, *J. Colloid Interface Sci.*, 49:410-421 (1974) (carboxylic acids on copper); Iler, *The Chemistry Of Silica*, Chapter 6, (Wiley 1979) (carboxylic acids on silica); Timmons and Zisman, *J. Phys. Chem.*, 69:984-990 (1965) (carboxylic acids on platinum); Soriaga and Hubbard, *J. Am. Chem. Soc.*, 104:3937 (1982) (aromatic ring compounds on platinum); Hubbard, *Acc. Chem. Res.*, 13:177 (1980) (sulfolanes, sulfoxides and other functionalized solvents on platinum); Hickman et al., *J. Am. Chem. Soc.*, 111:7271 (1989) (isonitriles on platinum); Maoz and Sagiv, *Langmuir*, 3:1045 (1987) (silanes on silica); Maoz and Sagiv, Langmuir, 3:1034 (1987) (silanes on silica); Wasserman et al., *Langmuir*, 5:1074 (1989) (silanes on silica); Eltekova and Eltekov, *Langmuir*, 3:951 (1987) (aromatic carboxylic acids, aldehydes, alcohols and methoxy groups on titanium dioxide and silica); Lec et al., *J. Phys. Chem.*, 92:2597 (1988) (rigid phosphates on metals).

The contacting of the oligonucleotide-modified composite particle with the target compound takes place under conditions effective for hybridization of the oligonucleotide on the oligonucleotide-modified composite particle with the target sequence of the target oligonucleotide. "Hybridization" means an interaction between two strands of nucleic acids by hydrogen bonds in accordance with the rules of Watson-Crick DNA complementarity, Hoogstein binding, or other sequence-specific binding known in the art. Hybridization can be performed under different stringency conditions known in the art. These hybridization conditions are well known in the art and can readily be optimized for the particular system employed. See, e.g., Sambrook et al., *Molecular Cloning: A Laboratory Manual* (2nd ed. 1989). Preferably stringent hybridization conditions are employed. Under appropriate stringency conditions, hybridization between the two complementary strands could reach about 60% or above, about 70% or above, about 80% or above, about 90% or above, about 95% or above, about 96% or above, about 97% or above, about 98% or above, or about 99% or above in the reactions.

Faster hybridization can be obtained by freezing and thawing a solution containing the oligonucleotide to be detected and the oligonucleotide-modified composite particles. The solution may be frozen in any convenient manner, such as placing it in a dry ice-alcohol bath for a sufficient time for the solution to freeze (generally about 1 minute for 100 µL of solution). The solution must be thawed at a temperature below the thermal denaturation temperature, which can conveniently be room temperature for most combinations of oligonucleotide-modified composite particles and target oligonucleotides. The hybridization is complete, and the detectable change may be observed, after thawing the solution. The rate of hybridization can also be increased by warming the solution containing the target compound and the oligonucleotide-modified composite particle to a temperature below the dissociation temperature ($T_m$) for the complex formed between the oligonucleotide on oligonucleotide-modified composite particle and the target compound. Alternatively, rapid hybridization can be achieved by heating above the dissociation temperature ($T_m$) and allowing the solution to cool. The rate of hybridization can also be increased by increasing the salt concentration (e.g., from 0.1 M to 0.3 M sodium chloride).

In other embodiments of the invention, methods are provided which are variations of the methods disclosed in WO 2005/003394, published Jan. 13, 2005, and United States Patent Application 20050277205, published Dec. 15, 2005, the disclosures of which of are incorporated by reference in their entirety. In variations of the methods disclosed therein, one or more of the particles used in the methods described are replaced with a composite particle of the invention. Specifically, the inventions described in WO 2005/003394 and 20050277205 utilize a magnetic particle as a capture phase wherein the magnetic particle has a moiety joined thereto that forms a specific binding pair with a first feature of a target analyte, thereby allowing the magnetic particle to bind with specificity to the target analyte thus forming a complex. Application of a magnetic field to a suspension of the magnetic particles and target analyte in a fluid allows the complexes comprised of target analyte bound to the magnetic particles to be separated from the fluid and any contaminants contained therein. The composite particles of the present invention may be employed for this purpose in the same manner as the magnetic particles of the prior art. Composite particles of the invention allow for consistency in size and shape in addition to having an inert surface over previously known magnetic particles. In addition, the composite particles allow for higher ligand density, are more stable and are less prone to non-specific binding over magnetic particles known in the art. This magnetic separation may be practiced on an analytical scale as described in WO 2005/003394 or on a preparative scale as described in 20050277205.

In another embodiment of the invention, the composite particles of the present invention can be employed in conjunction with the "biobarcode" method described in WO 2005/003394 as an alternative label attached to the "barcode" oligonucleotides that are released into solution prior to detection. As described in WO 2005/003394, these released barcodes either each bear a detectable label such as a fluorescent moiety or are caused to hybridize to complementary oligonucleotides that are, in turn, attached to a substrate such as a glass slide or a gold nanoparticle. The composite particles of this invention can be used in place of the detectable label or the oligonucleotide-modified substrate. In the former instance, a composite particle is attached directly to each barcode. In the latter instance, the barcode is caused to hybridize to complementary oligonucleotides that are, in turn, attached to composite particles of the present invention. In both instances the use of composite particles permits the rapid and efficient separation of the released barcodes from the solution in preparation for detection.

Additional aspects and details of the invention will be apparent from the following examples, which are intended to be illustrative rather than limiting.

EXAMPLES

General Experimental Conditions/Protocols

The magnetic properties of the composite particles of the claimed invention were measure by SQUID magnetometry using a MPMS SQUID magnetometer (Quantum Design).

Melting analyses were carried out using a Cary 5000 UV-Vis-NIR spectrophotometer (Varian) equipped with a Peltier temperature controller (Varian). The melting process was monitored by measuring the change in extinction of the solution at 260, 600, 700, and 950 nm. The solution was stirred magnetically during the experiment, the temperature was increased from about 25° C. to about 60° C. at about 1° C./min, and the extinction was recorded every 0.2° C.

ζ-potential measurements were performed using a NANO-Zs Zetasizer (Malvern Instruments). Colloid solutions were diluted with water in a ratio of about 1:100. Measurements were taken in disposable cuvettes (Malvern Instruments) equipped with electrodes and a folded capillary.

Example 1

Synthesis of the Composite Particles

Synthesis of Hydrophobic $Fe_3O_4$

Hydrophobic $Fe_3O_4$ nanoparticles having an average diameter of 15 nm were synthesized by a seed-mediated growth method following the procedure developed by Sun et al, 126 *J. Am. Chem. Soc.*, 273 (2004). All chemicals, i.e., iron (III) acetylacetonate ($Fe(acac)_3$), 1,2-hexadecanediol, oleic acid, oleylamine, benzyl ether, absolute ethanol and hexane, were purchased from Aldrich Co. (Milwaukee, Wis.) and used as received.

Figure 2:
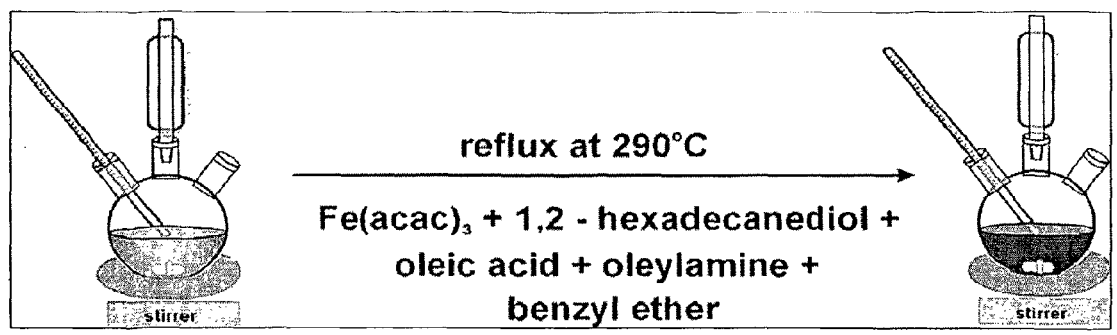
FIG. 2 illustrates the high-temperature synthesis of hydrophobic magnetite ($Fe_3O_4$) nanoparticles.

Initially, $Fe_3O_4$ seeds (9 nm) were synthesized by mixing 2 millimoles (mmol) $Fe(acac)_3$, 10 mmol 1,2-hexadecanediol, 6 mmol oleic acid, 6 mmol oleylamine, and 20 ml benzyl ether under a nitrogen atmosphere and heating the mixture at 200° C. for 2 hours while stirring under a slow flow of nitrogen. The nitrogen flow was stopped, and then the mixture was heated to reflux (about 290° C.) for 1 hour. The black-brown colored mixture was allowed to cool to room temperature, and stirring was maintained for an additional 4 hours (FIG. 2).

$Fe_3O_4$ (9 nm) nanoparticles were isolated by precipitating the particles with 40 ml of ethanol, followed by centrifugation at 10,000 rpm for 30 min. The black-brown precipitate was dissolved in 10 ml of hexane in the presence of 50 microliter (μL) oleic acid and 50 μL oleylamine, which formed a non-transparent black-brown colloid. Any particulate residue was removed by centrifugation at 6000 rpm for 10 min. The particles were again precipitated from the supernatant with 20 ml of ethanol, centrifuged at 10,000 rpm for 20 min, and redispersed in 10 ml of hexane.

Figure 3:
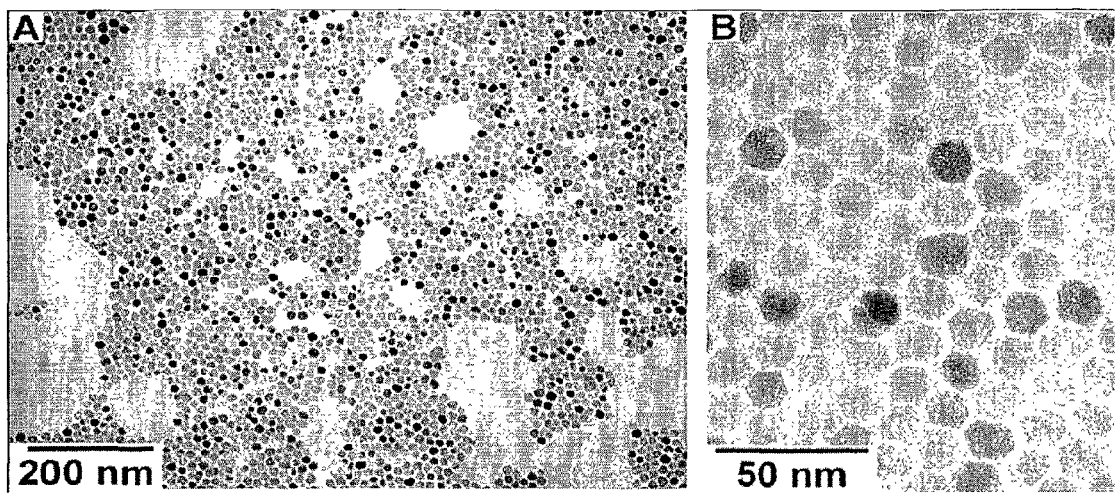
FIG. 3 contains transmission electron microscopy (TEM) images of 15 nanometer (nm) $Fe_3O_4$ nanoparticles in hexane.
Figure 4:
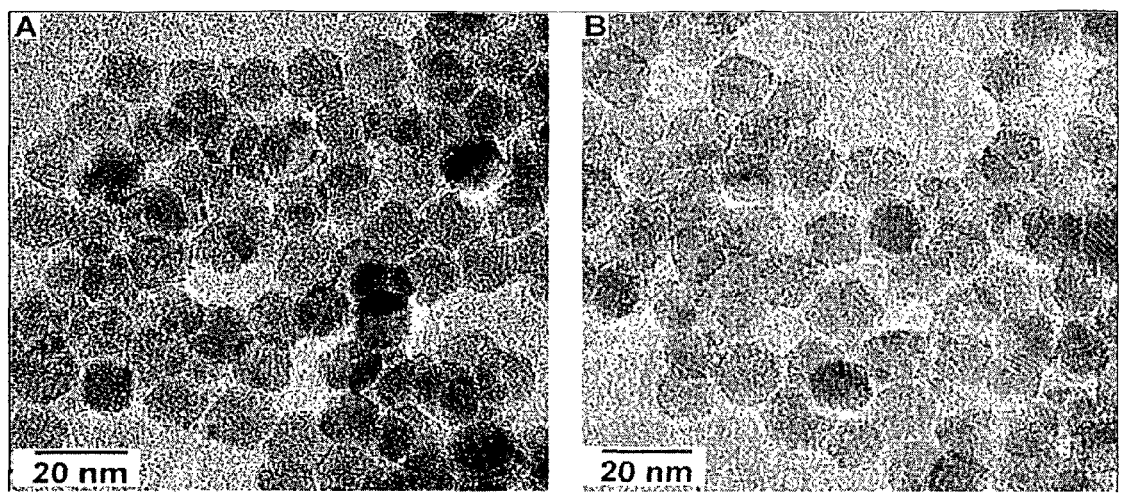
FIG. 4 contains TEM images of 15 nm $Fe_3O_4$ nanoparticles in water.

$Fe_3O_4$ (15 nm) nanoparticles were synthesized using a similar high-temperature growth procedure as the 9 nm $Fe_3O_4$ seeds. In particular, 2 mmol $Fe(acac)_3$, 10 mmol 1,2-hexadecanediol, 2 mmol oleic acid, 2 mmol oleylamine, and 10 ml benzyl ether were admixed under a nitrogen atmosphere. Five ml of the 9 nm $Fe_3O_4$ seeds in hexane was added to the mixture. The stirred mixture was heated under a flow of nitrogen to 100° C. to remove the hexane, then at 200° C. for 1 hour, and then at reflux for 30 min, all under a blanket of nitrogen. The final product (15 nm $Fe_3O_4$ nanoparticles) was isolated following the procedures for 9 nm $Fe_3O_4$ nanoparticles. The $Fe_3O_4$ colloid in hexane is stable for a long period of time (greater than 1 year). TEM images of these colloids are shown in FIG. 3 (in hexane) and FIG. 4 (in water).

Synthesis of Hydrophilic $Fe_3O_4$ Particles

Hydrophobic 15 nm $Fe_3O_4$ particles were transferred from a hexane to an aqueous solution using a bipolar surfactant (tetramethylammonium 11-aminoundecanoate).

Tetramethylammonium 11-aminoundecanoate was synthesized by titration of a methanolic suspension of 11-aminoundecanoic acid (4.04 grams (g) in approximately 4 ml methanol, Aldrich) with methanolic tetramethylammonium hydroxide (8.4 ml, Aldrich), evaporation of the solvent under reduced pressure, and recrystallization from tetrahydrofuran (about 50 ml, Aldrich).

For the phase transfer process, the surfactant (0.03 g) was suspended in about 2.5 ml dichloromethane (Aldrich), and 100 μL 15 nm hydrophobic $Fe_3O_4$ colloid was added. The resulting brown mixture was placed on a shaker for 2 hours, resulting in complete precipitation of the particles. The precipitated $Fe_3O_4$ particles were separated using a magnet, and then redispersed in Nanopure water (18 nm, Barnstead) resulting in a stable brown colloid. The particles were separated from excess surfactant by removing the supernatant after drawing the particles to a magnet, then redispersing the particles in Nanopure water.

Synthesis of Silica-Primed $Fe_3O_4$ Particles

Figure 5:
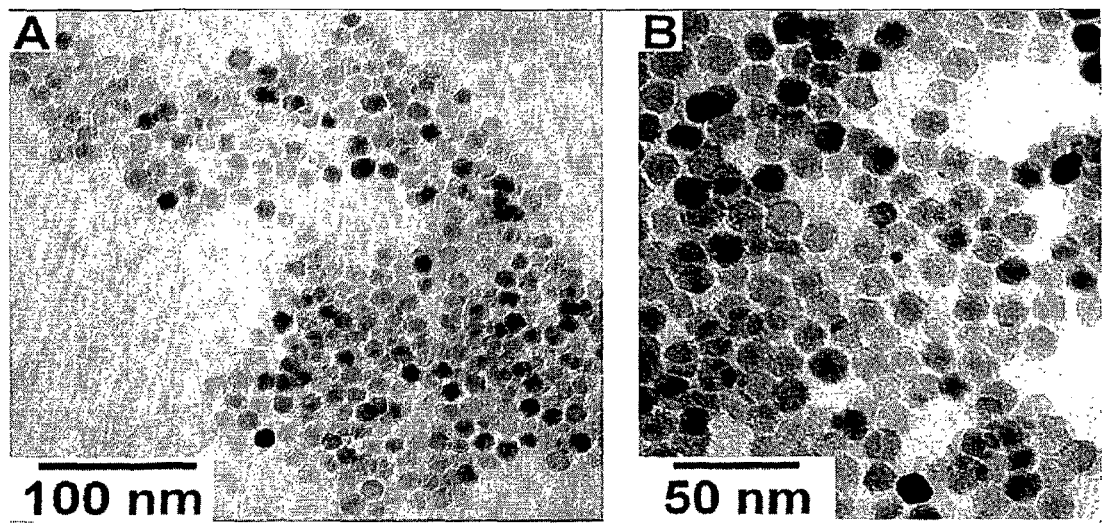
FIG. 5 contains TEM images of silica-primed 15 nm $Fe_3O_4$ nanoparticles.

Water-soluble $Fe_3O_4$ particles prepared by the procedure described above were primed with silica using a modified procedure. See Philipse et al., *Langmuir*, 10:92 (1994). A sodium silicate solution having pH about 10 was prepared by diluting 27 wt. % sodium silicate solution (Aldrich) with water. The sodium silicate solution was passed through a cation exchange resin (Amberlite, Aldrich) following the manufacturer's instructions. The pH of the sodium silicate solution after passing through the resin was approximately 5.5, and was quickly raised to 9-9.5 [using the original stock solution—Savka, is this correct? Yes, it is.]. The sodium silicate solution (6 mL) was added under vortex to 15 ml aqueous $Fe_3O_4$ colloid with the pH adjusted to 9-9.5 using a 0.25 wt. % aqueous solution of tetramethylammonium hydroxide (Aldrich). The resulting solution was placed on a shaker for 1 day at room temperature. The silica-primed $Fe_3O_4$ colloid was centrifuged at 2,500 rpm for 5 min to remove any aggregates, and the clear brown supernatant was separated. The silica-primed $Fe_3O_4$ particles were purified from excess silica by centrifugation at 10,000 rpm for 10 min twice, and finally redispersed into 10 ml Nanopure water. The average $\zeta$-potential of silica-primed $Fe_3O_4$ colloids at pH 7 was −35 mV. TEM images of these silica-primed particles are shown in FIG. 5.

Synthesis of 1-3 nm Gold Seeds

Gold seeds (1-3 inn) were synthesized by reduction of $HAuCl_4 \cdot 3H_2O$ with tetrakis(hydroxymethyl)phosphonium chloride (THPC). Sodium hydroxide (0.5 mL 1M solution) was added to 45 ml Nanopure water, followed by the addition of 1 ml THPC solution. The THPC solution was prepared by adding 12 μL of 80% THPC solution (Aldrich) to 1 ml of water. The mixture was stirred for 5 min, followed by quick addition of 1.5 ml of 1 wt. % $HAuCl_4 \cdot 3H_2O$ (Aldrich). The color of the solution turned brown over the course of 1 min. The solution was stirred for 15 min, then stored at 4° C. for 2-3 days.

Synthesis of Composite Particles a) $SiO_2$—$Fe_3O_4$—$Au_{seeds}$ Colloid

Figure 7:
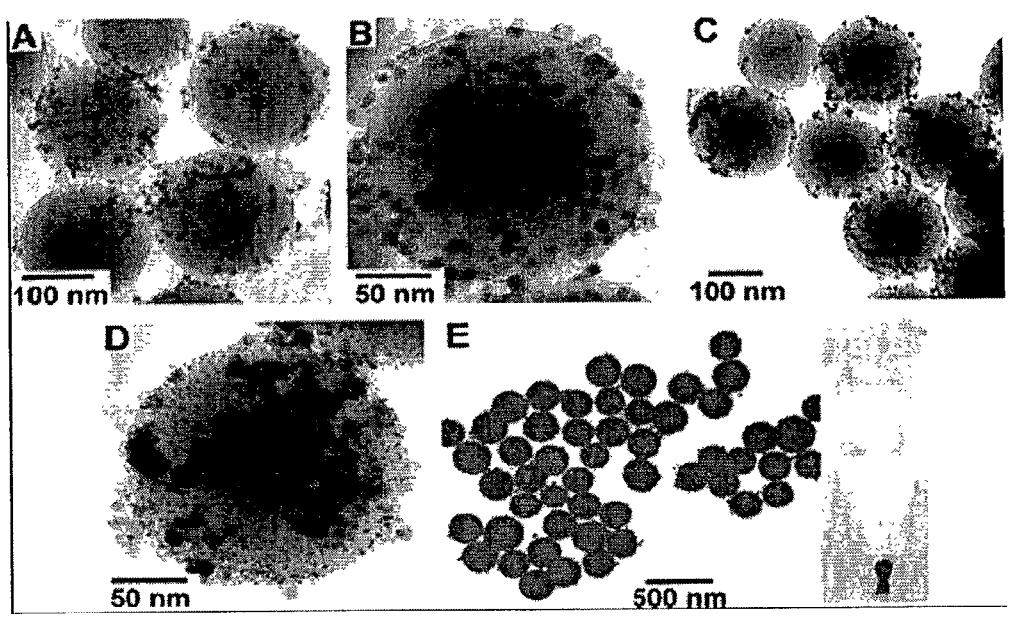
FIGS. 7A and B are TEM images of silica ($SiO_2$) particles covered with silica-primed $Fe_3O_4$ nanoparticles ($SiO_2$—$Fe_3O_4$)
FIGS. 7C and D are TEM images of $SiO_2$ particles covered with silica-primed $Fe_3O_4$ nanoparticles and heavily loaded with gold seeds ($SiO_2$—$Fe_3O_4$—$Au_{seeds}$)
FIG. 7E is a TEM image of composite particles synthesized in a single step process from the $SiO_2$—$Fe_3O_4$—$Au_{seeds}$ of FIGS. 7C and 7D, where the inset shows the composite particles drawn to the wall with a magnet.

In a typical experiment, 0.3 ml of 50 mg/ml amino-functionalized, 200 nm $SiO_2$ particles (Kicker) were diluted with 5.7 ml of Nanopure water. The average $\zeta$-potential of the $SiO_2$ colloid was +50 mV at pH 7. The $SiO_2$ colloid was slowly added under vortexing to 10 ml silica-primed $Fe_3O_4$ colloid with an average $\zeta$-potential −35 mV at pH 7. After 30 min, the colloid was centrifuged twice at 2,000 rpm for 5 min, then the brown pellet was redispersed in 6 ml Nanopure water. TEM images of the $SiO_2$—$Fe_3O_4$ colloids are shown in FIGS. 7A and 7B.

Next, 6 ml of the $SiO_2$—$Fe_3O_4$ colloid was added under vortexing to 30 ml of freshly prepared gold seed solution at pH 7 and mixed for 0.5 hour. After centrifugation at 5,100 rpm for 5 min, the brown-red precipitate $SiO_2$—$Fe_3O_4$—$Au_{seeds}$ was isolated and redispersed in 6 ml Nanopure water. The $SiO_2$—$Fe_3O_4$—$Au_{seeds}$ colloid was purified six times by suspension and centrifugation, then redispersed in water to ensure removal of free gold nanoparticles before the gold coating procedure. TEM images of the resulting colloids are shown in FIG. 7C and FIG. 7D.

b) Gold Shell Growth

Figure 6:
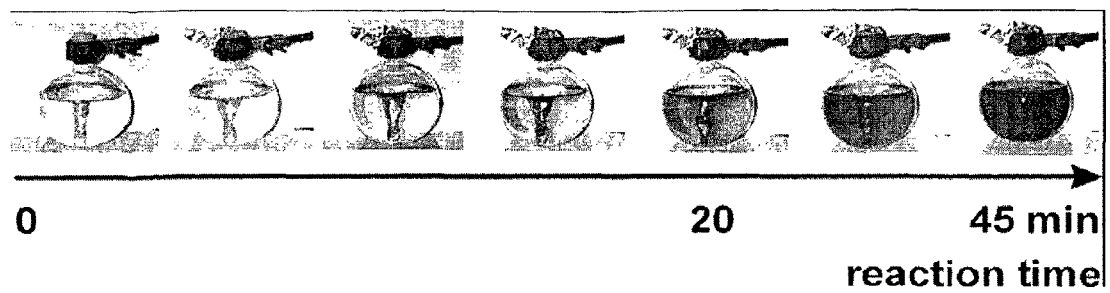
FIG. 6 illustrates the color change of the colloids over time during synthesis of the composite particles.

A continuous gold shell was grown around the $SiO_2$—$Fe_3O_4$—$Au_{seeds}$ particles by a one-step reduction of $HAuCl_4$ growth solution with formaldehyde (Aldrich). Selective deposition of gold on the $SiO_2$ particle surface was driven by the gold seeds acting as nucleation centers. $HAuCl_4$ growth solution was prepared one day in advance by adding 7.2 ml of 25 mg/ml $K_2CO_3$ solution to 720 ml Nanopure water, followed by the addition of 10.8 ml of 1 wt % $HAuCl_4$ solution. $SiO_2$—$Fe_3O_4$—$Au_{seeds}$ colloid (6 mL) was injected under stirring to 720 ml of the colorless $HAuCl_4$ growth solution. Next, formaldehyde (180 μL) was added to the vigorously stirred, colorless mixture leading to a gradual change of the reaction mixture color from colorless to purple to blue to red over 45 min. The blue color corresponded to the formation of gold shells, and the red color corresponded to the formation of free gold nanoparticles in solution. The composite particles were isolated by magnetic separation following repeated suspension and centrifugation at 2500 rpm for 3 min, then redispersed in Nanopure water. The final composite particles appeared red in reflected light and green in transmitted light. TEM images of the final composite particles are shown in FIG. 7E, where the inset shows that the particles are drawn to the side of a vessel when exposed to a magnet. FIG. 6 shows the darkening of a solution during the course of composite particle formation.

Example 2

Oligonucleotide Functionalization of the Composite Particle

Oligonucleotide Synthesis

All oligonucleotides were synthesized on a 1 micromole (μmol) scale using standard phosphoramidate chemistry on an automated DNA synthesizer (Milligene Expedite). All reagents required for the oligonucleotide synthesis were purchased from Glen Research. The 3'-thiol modified oligonucleotide was synthesized using 3'-thiol modifier C3 S—S CPG solid support. The 5'-thiol modified oligonucleotide was synthesized using 5'-thiol modifier C6 S—S phosphoramidite. All oligonucleotides were purified by reverse-phase HPLC (Hewlett Packard, 10×250 mm Varian DYNAMAX C18 column) with 1% per min gradient of 95% acetonitrile, and 5% 0.03 M triethylammonium (TEAA) pH 7 buffer. The retention times for the linker oligonucleotides and the 3'-thiol modified oligonucleotides were approximately 30 min and the retention time for the 5'-thiol modified oligonucleotides was approximately 50 mM. All oligonucleotides were stored at −20° C. in a lyophilized form prior to use and re-dissolved in Nanopure water when in use.

Functionalization of the Composite Particles with Oligonucleotides

Freshly synthesized composite particles were used for oligonucleotide functionalization. Before being added to the composite particles, the 3'-thiol-modified and 5'-thiol-modified oligonucleotide strands were deprotected by reaction in 0.1 M dithiothreitol (DTT, Pierce Biotechnology) in 0.17 M phosphate buffer pH 8 for 2 hours (10 OD of lyophilized oligonucleotide is typically deprotected with 150 μL 0.1M DTT solution). Aliquots of the deprotected oligonucleotide solution were purified through a desalting NAP-5 column (GE Healthcare), and the amount of oligonucleotide in each column fraction was determined by reading the absorbance of the solution at 260 nm.

Figure 9:
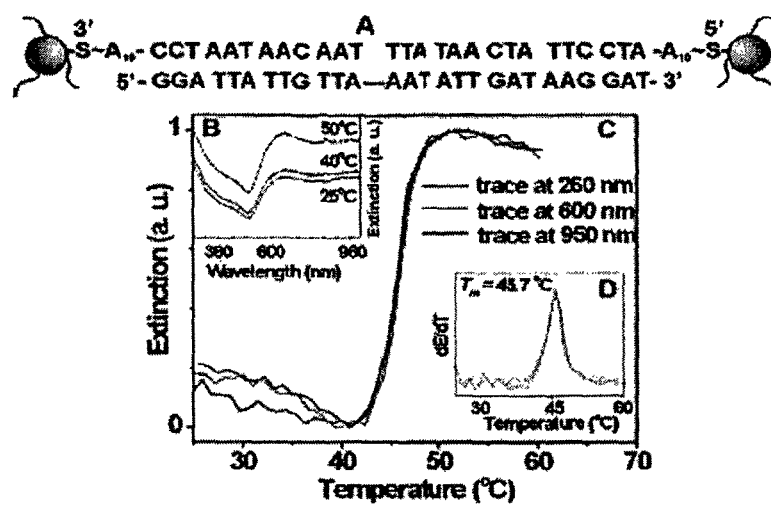
FIG. 9A is a schematic of the oligonucleotides used in the melting experiments.
FIG. 9B is a UV-Vis spectra of hybridized oligonucleotide modified composite particles (25 degrees Celsius (° C.)) and dispersed particles (50° C.)
FIG. 9C is a plot of extinction v. temperature (° C.) for aggregates formed from hybridized oligonucleotide-modified composite particles.
FIG. 9D is a plot of dE/dT v. temperature (° C.) for aggregates formed from hybridized oligonucleotide-modified composite particles.

Composite particles were functionalized with oligonucleotides by adding freshly deprotected oligonucleotide solution to the colloid (final concentration of oligonucleotides 30-40 micromolar (μM)). Two sets of colloids (a and b) were functionalized with 3'- and 5'-thiol-modified oligonucleotides, respectively. FIG. 9A shows a schematic of the two different colloids synthesized, together with a target nucleotide.

Figure 8:
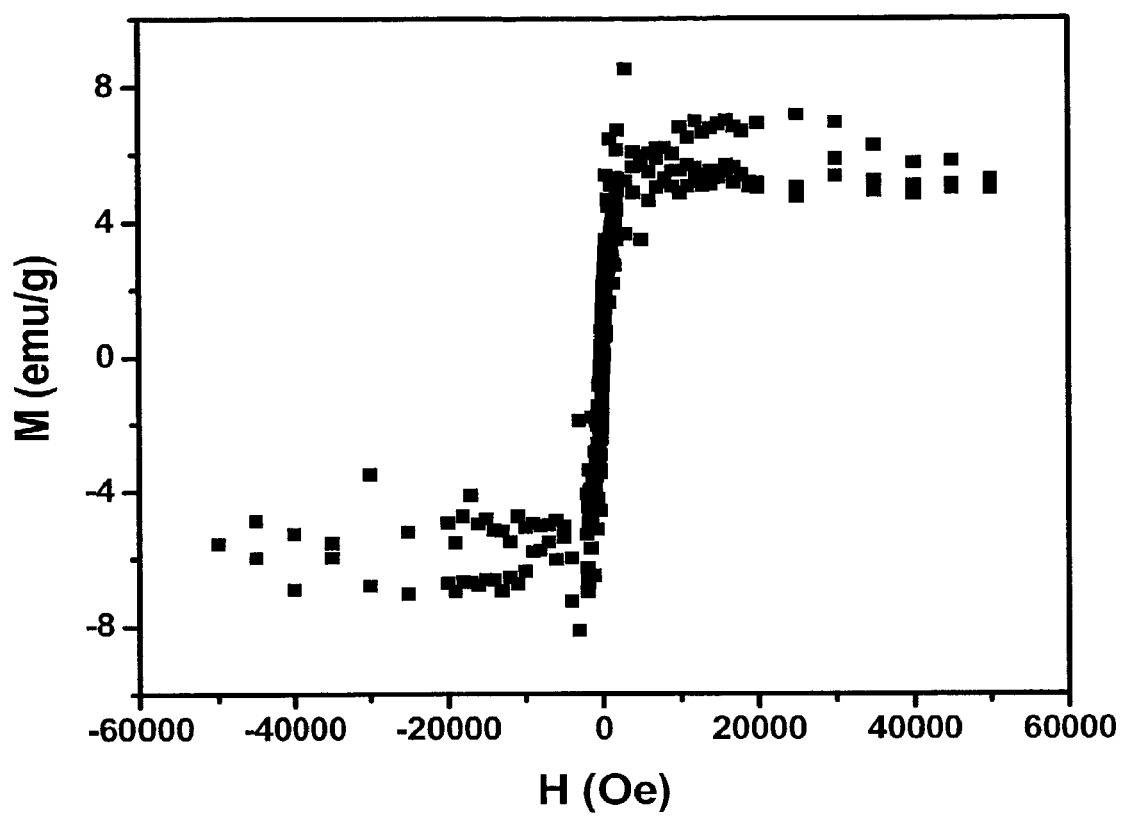
FIG. 8 is a plot of the hysteresis loop of the composite particles measured at 50 Kelvin (K)

The colloids were left undisturbed for approximately 16 hours, then brought to 10 millimolar (mM) phosphate concentration by adding 0.1 M phosphate buffer pH 7.4. This was followed by a slow salt aging process over approximately 2 days to a final salt concentration 0.1 M sodium chloride (NaCl). The salting process is carried out slowly in stepwise fashion to prevent aggregation of the colloids. After the salting was finished, the colloids were left undisturbed for approximately 1 day and purified from excess oligonucleotide by centrifugation at 3,000 rpm for 10 min (4 times) and re-dispersion in 0.1 M NaCl, 0.005% Tween 20, 10 mM phosphate buffer saline, pH 7.4. The resulting colloid was measured using SQUID magnetometry measurements at 50 K. The hysteresis loop shown in FIG. 8 indicates that the colloid is superparamagnetic and the net magnetization in the absence of an external magnetic field is zero.

Hybridization of Oligonucleotide-Modified Composite Particles with Target Linker The two colloids (a and b, synthesized above) in 0.1 M NaCl, 0.005% Tween 20, 10 mM phosphate buffer saline pH 7.4 were mixed in 1:1 ratio (~150 femtomole (fmol) of each), and 6 picomole (pmol) of target oligonucleotide (see FIG. 9A) was added to the solution. The colloid was left overnight at room temperature to ensure hybridization. The resulting hybridized composition of a, b, and the target oligonucleotide was then tested for its ability to melt, or reversibly release the target oligonucleotide, by monitoring the UV-Vis spectrum over a range of temperatures (FIG. 9B) and the extinction of the solution as a function of temperature (FIG. 9C). The first derivative of the melting curves shown in FIG. 9C are shown in FIG. 9D, indicated a sharp melting transition, typical of a cooperative melting effect in aggregates of nanoparticles heavily functionalized with DNA (Jin et al., *J. Am. Chem. Soc.*, 125:1643 (2003)).

Example 3

Synthesis of a Photonic Crystal

One mL composite particles (concentration 3 mg/mL) are dispersed in water and placed in a glass vial. The vial is covered with a cover having holes. The vial is placed in an incubator at 40° C. for 5 days, with no shaking. The solvent slowly evaporates and leaves dry, cracked crystals which can be used as photonic crystals.

All publications, patents and patent applications cited in this specification are herein incorporated by reference as if each individual publication or patent application were specifically and individually indicated to be incorporated by reference.

It will be understood that the invention has been described by way of example only and modifications may be made whilst remaining within the scope and spirit of the invention.

What is claimed:

1. A composite particle comprising a core and a gold shell, wherein the core comprises a dielectric component and a magnetic component, wherein the dielectric component is a surface-modified inorganic oxide, the gold shell is directly contacting the magnetic component and the dielectric component is not surface modified with a natural or synthetic polymer.

2. The composite particle of claim 1 wherein the inorganic oxide is selected from the group consisting of silica ($SiO_2$), $Nb_2O_5$, $Cr_2O_3$, $ZrO_2$, ZnO, CdO, $CeO_2$, $WO_3$, $Al_2O_3$ (alumina), $TiO_2$ (titania), and mixtures thereof.

3. The composite particle of claim 1 wherein the magnetic component comprises $Fe_3O_4$, FePt, $CoFe_2O_4$, $M*Fe_2O_4$, or a surface modified version thereof, wherein M* is a divalent cation.

4. The composite particle of claim 1 further comprising at least one oligonucleotide, wherein the oligonucleotide is bound to the gold shell.

5. The composite particle of claim 4 wherein the oligonucleotide is bound to the gold shell via a thiol moiety.

6. The composite particle of claim 1, wherein the magnetic component comprises iron.

7. The composite particle of claim 1, wherein the surface modified inorganic oxide comprises amino-modified silica.

8. The composite particle of claim 1, wherein the gold shell is deposited on the magnetic component.

9. A method for identifying a target compound in a sample containing or suspected of containing said target compound comprising the steps of
   a) contacting the sample with (i) a first composite particle of claim 4, wherein the oligonucleotide of said first composite particle hybridizes to at least a first portion of the target compound and (ii) a second composite particle of claim 4, wherein the oligonucleotide of said second composite particle hybridizes to at least a second portion of the target compound, under conditions that permit complex formation between said oligonucleotide of said first composite particle and said first portion of said target compound and between said oligonucleotide of said second composite particle and said second portion of said target compound, and
   b) detecting the composite particles bound to said target compound, wherein said detecting identifies the target compound in the sample.

10. A method for identifying a target compound in a sample containing or suspected of containing said target compound comprising the steps of
   a) contacting the sample with a composite particle of claim 1, wherein the composite particle is modified on its surface with a moiety selected from the group consisting of an oligonucleotide, a polypeptide, a polymer, a polysaccharide, an antibody, a lectin, and an antigen, and wherein said moiety interacts with said target compound to form a complex;
   b) removing said complex formed in step (a) from the sample using a magnetic field; and
   c) identifying the target compound using an analytic technique.

11. A method for separating a target compound in a mixture comprising the steps of
   a) contacting the mixture with (i) a composite particle of claim 1, wherein the composite particle is modified on its surface with a moiety selected from the group consisting of an oligonucleotide, a polypeptide, a polymer, a polysaccharide, an antibody, a lectin, and an antigen, and wherein said moiety interacts with said target compound to form a complex with the target compound, and (ii) a detectable probe modified on its surface with a moiety selected from the group consisting of an oligonucleotide, a polypeptide, a polymer, a polysaccharide, an antibody, a lectin, and an antigen, and wherein said moiety interacts with said target compound to form a complex with the target compound, under conditions that allow the composite particle and detectable probe to form an aggregate with the target compound; and
   b) removing said aggregate formed in step (a) from the sample using a magnetic field, thereby separating the target compound from the mixture.

* * * * *